United States Patent

Tanigaichi et al.

[11] 4,022,755
[45] May 10, 1977

[54] CYANATO-GROUP-CONTAINING PHENOL RESIN

[75] Inventors: Mineaki Tanigaichi, Tokyo; Susumu Motoori, Kashiwa; Kazuo Noguchi, Matsudo, all of Japan

[73] Assignee: Mitsubishi Gas Chemical Company, Inc., Tokyo, Japan

[22] Filed: July 21, 1975

[21] Appl. No.: 597,715

[30] Foreign Application Priority Data

July 29, 1974 Japan .............................. 49-86723

[52] U.S. Cl. .............................. 260/59 R; 260/838
[51] Int. Cl.$^2$ ........................................ C08L 61/06
[58] Field of Search .......... 260/59 R, 838; 528/132

[56] References Cited

OTHER PUBLICATIONS

Chem. Absts: vol. 68 (1968) 30633e, "Cyanate Group–Containing Phenolic Resins," Farbenfabriken Bayer AG.
Chem. Absts: vol. 62 (1965) 16104f, "Cyanogen Bromide and an Acylating Agent;" Thyagarajan.
Chem. Absts: 72 (1970) 56233g; "Plastic Materials from Aromatic Cyanates and Poly–epoxides;" Farbenfabriken Bayer AG.

Primary Examiner—Edward M. Woodberry

Attorney, Agent, or Firm—Armstrong, Nikaido & Marmelstein

[57] ABSTRACT

A novel cyanato-group-containing phenol resin is produced by reacting a cyanogen halide in an inert organic solvent in the presence of a base with a phenol novolak comprising a mixture of polymers represented by the formula,

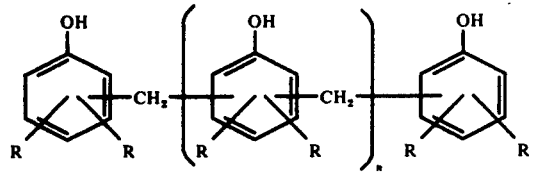

wherein, $n$ is 0 or an integer of 1 or more; and R's may be the same or different, and each R represents a hydrogen atom or a methyl group, and containing 50 % by weight or more in total of polymers having the above formula in which $n$ is an integer of 1 to 3, the number average molecular weight of said novolak being at least 300 and less then 600. This phenol resin is suitable for use in the production of a cured resin having outstanding thermal properties.

3 Claims, No Drawings

CYANATO-GROUP-CONTAINING PHENOL RESIN

This invention relates to a novel phenol resin containing cyanato groups and to a process for manufacturing the same. More particularly, this invention relates to a novel cyanato-group-containing phenol resin which is suitable for use in producing a cured resin having outstanding thermal properties, to a process for manufacturing the same, and to a composition comprising the same.

It has heretofore been known that a phenol resin containing cyanato groups is obtained by use of a phenol novolak having an average molecular weight of 600 to 1,500 in terms of hydroxy compound (for example, Japanese Patent Publication No. 11,712/70). However, the cured product from the phenol resin containing cyanato groups obtained by such a method is unsatisfactory in characteristics such as thermal properties.

An object of this invention is to provide a novel cyanato-group-containing phenol resin which is used for producing a cured product excellent in various characteristics, particularly in thermal properties.

Another object of this invention is to provide a process for manufacturing a novel cyanato-group-containing phenol resin.

A further object of this invention is to provide a resin composition comprising the abovesaid novel cyanato-group-containing phenol resin, other resins, and/or a filler.

Other objects and advantages of this invention will become apparent from the following description.

According to this invention, there is provided a cyanato-group-containing phenol resin comprising a mixture of polymers represented by the formula,

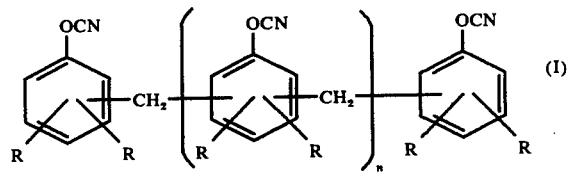

wherein $n$ is 0 or an integer of 1 or more; and R's may be the same or different, and each R represents a hydrogen atom or a methyl group, and containing 50% by weight or more in total of polymers having formula [I] in which $n$ is an integer of 1 to 3, the number average molecular weight of said phenol resin being in the range from 350 to 700, preferably 500 to 700, more preferably 550 to 650.

The above-said novel cyanato-group-containing phenol resin is manufactured, according to this invention, by reacting a cyanogen halide in an inert organic solvent in the presence of a base with a phenol novolak comprising a mixture of polymers represented by the formula,

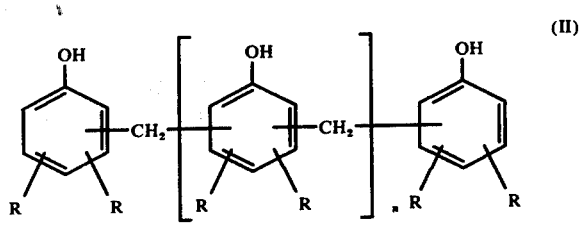

wherein $n$ and R have the same meanings as defined above, and containing 50% by weight or more in total of polymers having formula [II] in which $n$ is an integer of 1 to 3, the number average molecular weight of said phenol novolak being at least 300 and less than 600, preferably 400 to 550, more preferably 440 to 530. In this reaction the phenolic hydroxyl group is substantially 100% converted into the cyanato group.

The present resin forms networks upon heating and/or in the presence of a curing agent to be cured. Because of its high density of crosslinkage, the cured product is excellent in various characteristics such as, for example, thermal properties, and has a glass transition temperature of 300° C or higher.

It is essential for the manufacture of the present resin that there is used a phenol novolak comprising a mixture of polymers represented by the formula [II], and containing 50% by weight or more in total of polymers having the formula [II] in which $n$ is an integer of 1 to 3 (hereinafter, said phenol novolak is referred to simply as phenolic novolak). If the content of polymers having formula [II] in which $n$ is an integer of 1 to 3 is less than 50% by weight, the resulting cyanato-group-containing phenol resin gives a cured product inferior in thermal properties.

The phenolic novolak for use in this invention is obtained generally in the following way. To 100 moles of at least one phenol represented, for example, by the formula,

wherein R's have the same meanings as defined above), are added formalin ($CH_2O$ 37%) in an amount corresponding to 70 to 90 moles of formaldehyde and 0.1 to 1.0 mole of oxalic acid and/or hydrochloric acid in an amount corresponding to 0.05 to 0.5 mole of hydrogen chloride as catalyst. Oxalic acid and hydrogen chloride are preferably used together. The phenols may be used either alone or in combination of two or more. When the phenols are used in combination, they may be added in admixture previously prepared or each separately. The oxalic acid and/or hydrochloric acid may be added at the beginning or during the reaction, and also may be added alone or in admixture. Upon heating, the reactant mixture exhibits an emulsification phenomenon. After the emulsification has taken place, the primary reaction is allowed to proceed under reflux for 30 minutes to 5 hours. In order to carry out the secondary reaction, the reaction system is then heated under a reduced pressure of 10 to 300 mmHg for a further 2 to 8 hours while removing the water and unreacted components until the temperature of reaction system reaches 110° to 170° C, to obtain a viscous molten resin, which is then cooled to obtain a solid resin.

Examples of the phenols represented by the formula [III] include phenol, cresol, and xylenol.

The molecular weight distribution and number average molecular weight of the resin can be determined by gel permeation chromatography (GPC) using tetrahydrofuran as solvent.

The cyanogen halide to be used includes cyanogen chloride and cyanogen bromide, of which the former is preferred. The amount of the cyanogen halide used is 1 mole or more, preferably 1 to 2 moles, per mole of the phenolic hydroxyl group of the phenolic novolak to be converted into cyanato group. If the amount of cyanogen halide is less than 1 mole, some of the phenolic hydroxyl groups are not converted into cyanato groups.

The bases suitable for use are alkali metal hydroxides, alkaline earth metal hydroxides, alkali metal bicarbonates, alkali metal carbonates, alcoholates, and tertiary amines. Examples of typical bases suitable for use include sodium hydroxide, potassium hydroxide, calcium hydroxide, barium hydroxide, sodium bicarbonate, sodium carbonate, potassium carbonate, lithium carbonate, sodium methylate, trimethylamine, triethylamine, tripropylamine, and diethylcyclohexylamine. Of these, sodium hydroxide, potassium hydroxide, and triethylamine are preferred. The amount of the base used is 0.7 mole or more, preferably 1 to 2 moles, per mole of the phenolic hydroxyl group of the phenolic novolak to be converted into cyanato group. If the amount of the base is less than 0.7 mole, the rate of reaction becomes too small to be practicable.

The inert organic solvents used include hydrocarbons, chlorohydrocarbons, nitrohydrocarbons, ketones, and ethers. Examples thereof are benzene, toluene, xylene, chloroform, methylene chloride, carbon tetrachloride, chlorobenzene, nitrobenzene, nitromethane, acetone, methyl ethyl ketone, methyl isobutyl ketone, diethyl ether, tetrahydrofuran, and dioxane. Of these, acetone, methyl ethyl ketone, and dioxane are preferred.

The reaction according to this invention proceeds independently of the order of addition of components to the reaction system, so long as the amount of the base present in the system is always less than equivalent to the cyanogen halide. In a general practice, however, a phenolic novolak and a cyanogen halide are dissolved in a solvent and a base is added dropwise to the resulting solution while the solution is thoroughly stirred. The reaction temperature is preferably −30° to 65° C, particularly preferably 0° to 20° C. The objective resin is obtained from the reaction mixture, which has been freed from the by-product salt, by removing the solvent under reduced pressure or by adding dropwise said reaction mixture to a poor solvent for the resin. The IR spectrum of the resin thus obtained shows that phenolic hydroxyl groups of the starting resin have substantially 100% be converted to cyanato groups.

The present cyanato-group-containing phenol resin has a wide range of application fields such as manufacture of surface coating materials, cast plastics, adhesives, laminates, and molding materials. For these purposes, the resin is used as such or in combination with other cyanic esters, other polymers, fillers, or reinforcing materials, or catalysts.

The invention is illustrated below in detail with reference to Examples, but the invention is not limited thereto. In the Examples, all parts and percentages are by weight, unless otherwise specified.

EXAMPLE 1

To a mixture of 160 g (1.70 moles) of phenol and 100 g (1.23 moles as $CH_2O$) of formalin (37% $CH_2O$) were added 0.80 g (0.0089 mole) of oxalic acid and 0.3 g (0.0029 mole as HCl) of hydrochloric acid (35%) as catalysts. The mixture was heated at 99° to 100° C to form an emulsion. The emulsion was subjected to reaction under reflux for 80 minutes and then dehydrated under reduced pressure to obtain a solid phenol novolak. The resulting phenol novolak having a melting point of 62° to 68° C contained 16% in total of the unreacted phenol and a polymer having $n = 0$, 75% in total of polymers having $n = 1, 2$ and $3$, and 9% in total of polymers having $n \geq 4$ in the formula [II], and had a number average molecular weight of 380, as measured by GPC using tetrahydrofuran as solvent.

In 210 ml of methyl ethyl ketone was dissolved 42 g (0.396 mole as —OH) of the above phenol novolak. To the resulting solution, which had been cooled to 0° C, was added 46 g (0.434 mole) of cyanogen bromide. After dropwise addition of 42 g (0.415 mole) of triethylamine with thorough stirring, the reaction temperature was maintained at 5° to 10° C. After completion of the reaction, the by-product triethylamine-hydrogen bromide salt was removed by suction filtration. The filtrate was concentrated under reduced pressure to obtain a solid phenol resin containing cyanato groups, which had a melting point of 45° to 52° C and a number average molecular weight of 480 according to GPC, and was soluble in methyl ethyl ketone. The phenol resin contained 15% in total of mononuclear compound and a polymer having $n = 0$, 76% in total of polymers having $n = 1, 2$ and $3$ and 9% in total of polymers having $n \geq 4$ in the formula [I] according to GPC.

By IR absorption spectroscopy conducted on the resulting phenol resin, it was found that the absorption at about 3400 $cm^{-1}$ due to the phenolic hydroxyl group had disappeared, and an absorption at 2250 $cm^{-1}$ characteristic of the cyanato group had appeared, indicating that the hydroxyl groups had substantially 100% been converted to cyanato groups.

A cured product obtained from the cyanato-group-containing phenol resin thus prepared by melt-molding at 150° C and thereafter curing thoroughly at 200° C was found to have a glass transition temperature higher than 300° as a result of the measurement of thermal expansion coefficient.

EXAMPLE 2

The procedure of Example 1 was repeated, except that 27 g (0.439 mole) of cyanogen chloride was substituted for 46 g (0.434 mole) of cyanogen bromide, to obtain a resin having a glass transition temperature higher than 300° C, which was similar to that of Example 1.

EXAMPLE 3

To a mixture of 150 g (1.59 moles) of phenol and 110 g (1.36 moles as $CH_2O$) of formalin (37% $CH_2O$) were added 0.75 g (0.0083 mole) of oxalic acid and 0.3 g (0.0029 mole as HCl) of hydrochloric acid (35%) as catalyst. The mixture was heated at 99° to 100° C to form an emulsion. The emulsion was subjected to reaction under reflux for 75 minutes and then dehydrated under reduced pressure to obtain a solid phenol novolak. The resulting phenol novolak having a melting point of 85° to 93° C contained 11% in total of the unreacted phenol and a polymer having $n = 0$, 64% in total of polymers having $n = 1, 2$ and $3$, and 25% in total of polymers having $n \geq 4$ in the formula [II] and had a number average molecular weight of 430 according to GPC.

The thus obtained phenol novolak was cynated in the same manner as in Example 1. After removal of the triethylamine salt by filtration, the reaction mixture was added dropwise to vigorously stirred water to obtain a cyanato-group-containing phenol resin in the form of a powder. After drying, the resulting resin in the powder form showed a melting point of 63° to 67° C and had a number average molecular weight of 540 according to GPC. The phenol resin contained 64% in total of polymers having $n = 1, 2$ and 3 in the formula [I] according to GPC. A strong absorption at 2250 $cm^{-1}$ in IR spectrum of the resin showed that the phenolic hydroxyl groups had substantially 100% been converted to cyanato groups. The cured product had a glass transition temperature higher than 300° C.

EXAMPLE 4

To a mixture of 108 g (0.999 mole) of m-cresol and 65 g (0.801 mole as $CH_2O$) of formalin (37% $CH_2O$) were added 0.2 g of (0.0022 mole) oxalic acid and 0.1 g (0.0010 mole as HCl) of hydrochloric acid (35%) as catalyst. The mixture was heated at 99° to 100° C to form an emulsion. The emulsion was then subjected to reaction under reflux for 4 hours and 30 minutes and then dehydrated under reduced pressure to obtain a solid cresol novolak. The resulting cresol novolak having a melting point of 92° to 103° C contained 65% in total of polymers having $n = 1, 2$ and 3 in the formula [II], and had a number average molecular weight of 550 according to GPC.

In 210 ml of acetone was dissolved 72 g (0.6 mole as —OH) of the m-cresol novolak obtained above. To the resulting solution, which had been cooled to 0° C, was added 70 g (0.661 mole) of cyanogen bromide, followed by dropwise addition of 64 g (0.632 mole) of triethylamine. After completion of the reaction, the triethylamine-hydrogen bromide salt was removed. The resulting reaction mixture was added to vigorously stirred water to obtain a resin in the form of a powder which had a melting point of 74° to 77.5° C. The resin contained 64% in total of polymer having $n = 1, 2$ and 3 in the formula [I] and had a number average molecular weight of 640 according to GPC. A strong absorption at 2250 $cm^{-1}$ in IR spectrum of the resin showed that the phenolic hydroxyl groups had substantially 100% been converted to cyanato groups. The glass transition temperature of the cured molded article was above 300° C.

EXAMPLE 5

To a mixed solution of 122 g (0.999 mole) of 3,5-xylenol and 61 g (0.752 mole as $CH_2O$) of formalin (37% $CH_2O$) were added 0.16 g (0.0018 mole) of oxalic acid and 0.1 g (0.0010 mole as HCl) of hydrochloric acid (35%) as catalyst. The mixture was heated at 90° C to form an emulsion. The emulsion was subjected to reaction at 90° C for 2 hours and then dehydrated under reduced pressure of 60 mmHg until the temperature reached 160° C to obtain a solid xylenol novolak having a melting point of 90° to 98° C. The resulting xylenol novolak contained 72% in total of polymers having $n = 1, 2$ and 3 in the formula [II], and had a number-average molecular weight of 520 according to GPC.

In 250 ml of acetone was dissolved 67 g (0.5 mole as —OH) of the above xylenol novolak. To the resulting solution, which had been cooled to 0° C, was added 34 g (0.553 mole) of cyanogen chloride, followed by dropwise addition of 53 g (0.524 mole) of triethylamine. After the reaction had been complete, the by-product triethylamine-hydrogen chloride salt was removed by filtration. The resulting reaction mixture was added to vigorously stirred water to obtain a resin in the powder form, which had a melting point of 68° to 77° C. A strong absorption at 2250 $cm^{-1}$ in IR spectrum of the resin showed that the phenolic hydroxyl groups had substantially 100% been converted to cyanato groups. The cured molded article had a glass transition temperature of 260° C.

EXAMPLE 6

To a mixed solution of 47 g (0.499 mole) of phenol and 69 g (0.850 mole as $CH_2O$) of formalin (37% $CH_2O$) were added 0.36 g (0.0040 mole) of oxalic acid and 0.1 g (0.0010 mole as HCl) of hydrochloric acid (35%) as catalyst. After having been emulsified by heating at 99° to 100° C, the mixture was subjected to reaction under reflux for 30 minutes, and 54 g (0.499 mole) of m-cresol was added thereto, after which the reaction was continued for a further 30 minutes under reflux. The reaction mixture was dehydrated under a reduced pressure of 60 mmHg until the temperature reached 160° C to obtain a solid phenol novolak having a melting point of 85° to 91° C. The resulting phenol novolak contained 66% in total of polymers having $n = 1, 2$ and 3 in the formula [II], and had a number average molecular weight of 490 according to GPC.

In 250 ml of methyl ethyl ketone was dissolved 45 g (0.398 mole as —OH) of the above phenol novolak. To the resulting solution, which had been cooled to 0° C, was added 47 g (0.444 mole) of cyanogen bromide, followed by dropwise addition of 43 g (0.425 mole) of triethylamine. After completion of the reaction, the resulting triethylamine-hydrogen bromide salt was removed by filtration. The resulting reaction mixture was concentrated under reduced pressure to obtain a solid resin having a melting point of 53° to 65° C. A strong absorption at 2250 $cm^{-1}$ in IR spectrum of the resin showed that the phenolic hydroxyl groups had substantially 100% been converted to cyanato groups. The glass transition temperature of the cured molded article was higher than 300° C.

EXAMPLE 7

In 250 ml of methyl ethyl ketone were dissolved 21 g (0.198 mole as —OH) of the phenol novolak obtained in Example 1 and 24 g (0.20 mole) of the m-cresol novolak obtained in Example 4. To the resulting solution, which had been cooled to 0° C was added 47 g (0.444 mole) of cyanogen bromide, followed by dropwise addition of 43 g (0.425 mole) of triethylamine. After completion of the reaction, the by-product triethylamine-hydrogen bromide salt was removed by filtration and the resulting reaction mixture was concentrated under reduced pressure to obtain a solid resin having a melting point of 49° to 61° C. A strong absorption at 2250 $cm^{-1}$ in the IR spectrum of the resin showed that the phenolic hydroxyl groups had substantially 100% been converted to cyanato groups. The glass transition temperature of the cured molded article was higher than 300° C.

EXAMPLE 8

To a solution of 42 g (0.396 mole as —OH) of the phenol novolak obtained in Example 3 in 210 ml of dioxane, after having been cooled to 0° C, was added 46 g (0.434 mole) of cyanogen bromide. To the resulting mixture, while being thoroughly stirred was added gradually 16.4 g (0.41 mole) of powdered sodium hydroxide and the reaction temperature was kept at 5° to 10° C. The reaction product showed substantially the same properties as those of the cyanato-group-containing phenol resin obtained in Example 3. The cured molded article from the said reaction product had also substantially the same characteristics as those of the cured article obtained in Example 3.

COMPARATIVE EXAMPLE 1

To 1,880 g (19.98 moles) of phenol heated at 90° C were added dropwise 1,265 g (15.59 moles as $CH_2O$) of formalin (37% $CH_2O$) and 50 g (0.555 mole) of oxalic acid over a period of 2 hours. Thereafter, the reaction was allowed to proceed at 90° C for 8 hours. The reaction mixture was cooled to 40° C, separated from the aqueous layer, washed with 300 ml of hot water, and then dehydrated under reduced pressure of 40 mmHg until the temperature reached 160° C to obtain a solid phenol novolak. The above procedure was in accordance with the description in "Methoden der organischen Chemie, Vol. 14/2, S, 273, Beispiel 2." The thus obtained phenol novolak having a softening point of 124° C contained 3% in total of the unreacted phenol and a polymer having $n = 0$, 23% in total of polymers having $n = 1, 2$ and 3, and 74% in total of polymers having $n \geq 4$ in the formula [II] and had a number average molecular weight of 850 according to GPC.

The above phenol novolak was cyanated in the same way as in Example 1 to obtain a resin in the powder form, which showed no definite melting point, and had a number average molecular weight of 1,050 according to GPC. The resin contained 25% in total of polymers having $n \leq 3$ and 75% in total of polymers having $n \geq 4$ in the formula [I] according to GPC. Although a strong absorption was observed at 2250 $cm^{-1}$, the IR spectrum showed residual phenolic hydroxyl groups in the resin. A cured molded article from the resin had a glass transition temperature of 248° C.

COMPARATIVE EXAMPLE 2

To a mixed solution of 180 g (1.913 moles) of phenol and 90 g (1.109 moles as $CH_2O$) of formalin (37% $CH_2O$) was added 0.96 g (0.011 mole) of oxalic acid as catalyst and the resulting mixture was heated at 80° C to form an emulsion. The emulsion was subjected to reaction at 80° C for 30 minutes, and then dehydrated at 100° C under reduced pressure until the pressure reached 30 mmHg to obtain a phenol novolak in the form of a semi-solid at room temperature. The resulting phenol novolak contained 62% in total of the unreacted phenol and a polymer having $n = 0$, 37% in total of polymers having $n = 1, 2$ and 3, and 1% in total of polymers having $n \geq 4$ in the formula [II] and had a number average molecular weight of 220 according to GPC.

The phenol novolak thus obtained was cyanated in the same manner as in Example 1 to obtain a semisolid cyanato-group-containing phenol resin. The IR spectrum of the resin showed a strong absorption at 2250 $cm^{-1}$ and disappearance of the absorption due to the phenolic hydroxyl group. The glass transition temperature of a cured molded product from the resin was found to be 225° C as a result of the measurement of thermal expansion coefficient.

COMPARATIVE EXAMPLE 3

Equal amounts of the phenol novolak used in Comparative Example 1 and that used in Comparative Example 2 were dissolved in methyl ethyl ketone and mixed. By calculation, the mixed phenol novolak should have contained 32.5% in total of the unreacted phenol and a polymer having $n = 0$, 30% in total of polymers having $n = 1, 2$ and 3, and 37.5% in total of polymers having $n \geq 4$ in the formula [II], and should have had a number average molecular weight of 350.

The mixed phenol novolak was cyanated in the same manner as in Example 1 to obtain a cyanato-group-containing phenol resin, which had a melting point of 42° to 56° C. A cured molded product obtained from the said phenol resin was found to have a glass transition temperature of 242° C as a result of the measurement of thermal expansion coefficient.

COMPARATIVE EXAMPLE 4

Equal amounts of the phenol novolak used in Example 1 and that used in Comparative Example 3 were dissolved in methyl ethyl ketone and mixed. By calculation, the mixed phenol novolak should have contained 39% in total of the unreacted phenol and a polymer having $n = 0$, 56% in total of polymers having $n = 1, 2$ and 3, and 5% in total of polymers having $n \geq 4$ in the formula [II], and should have had a number average molecular weight of 280.

The mixed phenol novolak was cyanated in the same manner as in Example 1 to obtain a cyanato-group-containing phenol resin, which had a melting point of 31° to 43° C. A cured molded product obtained from this phenol resin was found to have a glass transition temperature of 247° C as a result of the measurement of thermal expansion coefficient.

COMPARATIVE EXAMPLE 5

In 200 ml of acetone was dissolved 40 g (0.40 mole as —OH) of commercially available bishydroxybisphenylmethane. To the resulting solution, which had been cooled to 0° C, was added 46 g (0.434 mole) of cyanogen bromide, followed by dropwise addition of 42 g (0.415 mole) of triethylamine with thorough stirring. The reaction temperature was kept at 5° to 10° C. After completion of the reaction, the byproduct was removed by filtration and the filtrate was concentrated and then cooled to precipitate biscyanatobisphenylmethane in the crystal form. A strong absorption at 2250 $cm^{-1}$ in IR spectrum of the said substance showed that the phenolic hydroxyl groups had substantially 100% been converted into cyanato groups. The glass transition temperature of a cured molded product obtained from this substance was 194° C.

TEST EXAMPLE

In the following Table are shown moduli of elasticity at room temperature and at 250° C, which will serve as a measure of mechanical strength at high temperatures, as determined by dynamic visco-elasticity measurement conducted on the cyanato-group-containing phenol resins obtained in Examples 1 to 7 and Comparative Examples 1 and 5. These moduli of elasticity were obtained by the phase difference method (frequency: 11 Hz). In the following Table, a greater dynamic storage modulus (E') and smaller dynamic loss modulus (E'') mean a better mechanical strength.

Table

| | Dynamic storage modulus E' (dyne/cm$^2$) | | Dynamic loss modulus E'' (dyne/cm$^2$) | |
|---|---|---|---|---|
| | Room temp. | 250° C | Room temp. | 250° C |
| Example 1 | $2.2 \times 10^{10}$ | $1.6 \times 10^{10}$ | $2.9 \times 10^8$ | $4.4 \times 10^8$ |
| 2 | $2.2 \times 10^{10}$ | $1.6 \times 10^{10}$ | $2.9 \times 10^8$ | $4.3 \times 10^8$ |
| 3 | $2.2 \times 10^{10}$ | $1.5 \times 10^{10}$ | $2.4 \times 10^8$ | $3.0 \times 10^8$ |
| 4 | $2.2 \times 10^{10}$ | $1.5 \times 10^{10}$ | $2.9 \times 10^8$ | $4.8 \times 10^8$ |
| 5 | $2.1 \times 10^{10}$ | $1.3 \times 10^{10}$ | $2.9 \times 10^8$ | $8.6 \times 10^8$ |
| 6 | $2.2 \times 10^{10}$ | $1.6 \times 10^{10}$ | $2.8 \times 10^8$ | $4.5 \times 10^8$ |
| 7 | $2.2 \times 10^{10}$ | $1.6 \times 10^{10}$ | $2.7 \times 10^8$ | $4.5 \times 10^8$ |
| Comparative Example 1 | $2.2 \times 10^{10}$ | $1.2 \times 10^{10}$ | $3.1 \times 10^8$ | $12 \times 10^8$ |
| 5 | $2.1 \times 10^{10}$ | $1.1 \times 10^{10}$ | $3.5 \times 10^8$ | $15 \times 10^8$ |

As is apparent from Comparative Examples 1 to 4, there is obtained a cured molded article having a glass transition temperature below 250° C, indicating heat resistance inferior to that of the cured molded article of this invention, if one of the following phenol novolaks was used: (i) A phenolic novolak containing less than 50% by weight in total of polymers having $n = 1, 2$ and 3 in the formula [II] and having a number average molecular weight of 600 or more, (ii) a phenolic novolak containing less than 50% by weight in total of polymers having $n = 1, 2$ and 3 in the formula [II] and having a number average molecular weight lower than 300, (iii) a phenolic novolak containing less than 50% by weight in total of polymers having $n = 1, 2$ and 3 in the formula [II], and having a number average molecular weight of at least 300 and less than 600, and (iv) a phenolic novolak containing not less than 50% by weight in total of polymers having $n = 1, 2$ and 3 in the formula [II] and having a number average molecular weight lower than 300. There are practically not present phenol novolaks containing more than 50% by weight in total of polymers having $n = 1, 2$ and 3 in the formula [II] and having a number average molecular weight of 600 or more.

What is claimed is:

1. A cyanato-group-containing phenol resin comprising a mixture of polymers represented by the formula:

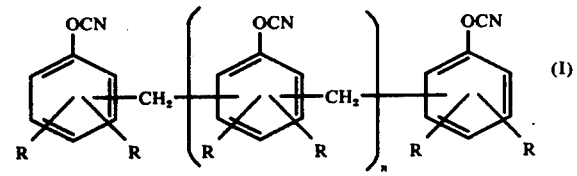

wherein $n$ is 0 or an integer of 1 or more; and R's may be the same or different, and each R is a hydrogen atom or a methyl group, and containing 50% by weight or more in total of polymers having formula in which $n$ is an integer of 1 to 3, the number average molecular weight of said phenol resin being 350 to 700, as determined by gel permeation chromatography using tetrahydrofuran as solvent.

2. A cyanato-group-containing phenol resin according to claim 1, wherein the number average molecular weight is 500 to 700.

3. A cyanato-group-containing phenol resin according to claim 1, wherein the number average molecular weight is 500 to 650.

* * * * *